United States Patent
Bondinell et al.

(10) Patent No.: US 6,221,860 B1
(45) Date of Patent: Apr. 24, 2001

(54) BETA-LACTAM INHIBITORS OF COA-IT

(75) Inventors: William E. Bondinell, Wayne; James David Winkler, Fort Washington, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/423,421

(22) PCT Filed: May 8, 1998

(86) PCT No.: PCT/US98/09485

§ 371 Date: Nov. 8, 1999

§ 102(e) Date: Nov. 8, 1999

(87) PCT Pub. No.: WO98/50032

PCT Pub. Date: Nov. 12, 1998

Related U.S. Application Data (60) Provisional application No. 60/046,080, filed on May 9, 1997.

(51) Int. Cl.[7] .......................... A01N 43/00; A01K 31/395
(52) U.S. Cl. .................. 514/210.02; 540/200; 540/354; 540/358; 540/359; 540/360; 540/364
(58) Field of Search ...................... 514/210.02; 540/200, 540/354, 358, 359, 360, 364

(56) References Cited

U.S. PATENT DOCUMENTS 4,647,558 * 3/1987 Ponsford et al. .................... 514/210

OTHER PUBLICATIONS

Chemical Abstracts 112:76713, "Synthesis of Novel 3–Formamido–3–(Acylamino)monobactams", Apr. 1989.*

* cited by examiner

*Primary Examiner*—Frederick Krass
(74) *Attorney, Agent, or Firm*—Dara L. Dinner; Stephen Venetianer; Charles M. Kinzig (57) ABSTRACT

This invention relates to methods for treating diseases or disorders mediated by lipid inflammatory mediators, arachidonic acid, its metabolites and/or platelet activating factor (PAF), which method comprises administration to a mammal in need thereof of an effective Coenzyme A independent transacylase (CoA-IT) inhibiting amount of a triphenylmethylazetidinone. This invention also relates to a method of treating or reducing inflammation in a mammal in need thereof, which comprises administering to said mammal an effective amount of a triphenylmethylazetidinone.

15 Claims, 4 Drawing Sheets

BETA-LACTAM INHIBITORS OF COA-IT

This application is a 371 of PCT/US 98/09483, filed May 8, 1998, and claims priority to provisional application 60/046,080, filed May 9, 1997.

FIELD OF THE INVENTION

This invention relates to novel compounds, pharmaceutical compositions thereof, and their use as anti-inflammatory agents in mammals.

BACKGROUND OF THE INVENTION

Coenzyme A-independent transacylase (CoA-IT) is an enzyme responsible for the movement of arachidonate between phospholipid molecular species of inflammatory cells. CoA-IT removes arachidonate from the sn-2 position of 1-acyl-containing phospholipids, such as 1-acyl-2-arachidonoyl-sn-glycero-3-phosphocholine (1-acyl-2-arachidonoyl-GPC). It then transfers that arachidonate to a suitable lyso-phospholipid acceptor, such as 1-alkyl-2-lyso-GPC and 1-alkenyl-2-lyso-sn-glycero-3-phosphoethanolamine (Sugiura et al., J. Biol. Chem. 262: 1199–1205 (1987); Kramer and Deykin, Biol. Chem. 258: 13806–13811 (1983); Chilton et al., J. Biol. Chem. 258: 7268–7271 (1983)). This activity is selective for 20 carbon fatty acyl groups and is the mechanism by which inflammatory cells move arachidonate into specific phospholipid pools prior to its release (Winkler and Chilton, Drug News Perspec. 6: 133–138 (1993); Snyder et al., J. Lipid Mediat. 10: 25–31 (1994)).

Further, a method which antagonises the production of free arachidonic acid, its metabolites or PAF will have clinical utility in the treatment of a variety of allergic, inflammatory and hypersecretory conditions such as asthma, arthritis, rhinitis, bronchitis and urticaria, as well as reperfusion injury and other disease involving lipid mediators of inflammation. Many published patent applications or issued U.S. patents exist which describe various compounds having utility as PAF or eicosanoid antagonists. Such patents include U.S. Pat. Nos. 4,788,205, 4,801,598, 4,981,860, 4,992,455, 4,983,592, 5,011,847, 5,019,581 and 5,002,941.

Accordingly, as CoA-IT is involved in arachidonic acid and phospholipid metabolism, inhibition of such an enzyme would be useful for the treatment of inflammatory, allergic and hypersecretory conditions or disease states caused thereby. Therefore, a method by which CoA-IT is inhibited will consequently and preferentially decrease the arachidonate content of 1-alkyl- and 1-alkenyl-linked phospholipids and will therefore decrease the production of pro-inflammatory mediators such as free arachidonic acid, prostaglandins, leukotriene and PAF during an inflammatory response.

There remains a need for treatment, in this field, for compounds which are CoA-IT inhibitors, i.e. compounds which are capable of inhibiting, or interfering with this enzyme and thereby decrease production of the pro-inflammatory mediators.

SUMMARY OF THE INVENTION

This invention also relates to a method of treating or reducing inflammation in a mammal in need thereof, which comprises administering to said mammal an effective amount of a compound or composition of Formula (I).

This invention also relates to a method of treating disease or disorders mediated by lipid inflammatory mediators, free arachidonic acid, its metabolites and/or PAF by administering to a patient in need thereof, an effective amount of a compound of Formula (I).

This invention also relates to a method of treating disease or disorders mediated by Coenzyme A independent transacylase (CoA-IT) by administering to a patient in need thereof, an effective amount of a compound or composition of Formula (I).

This invention relates to the novel compounds of Formula (Ia) and pharmaceutically acceptable salts thereof. The present invention also provides for a pharmaceutical composition comprising a pharmaceutical acceptable carrier or diluent and a compound of Formula (Ia), or pharmaceutically acceptable salt thereof.

One aspect of the present invention are the compounds represented by a structure having the formula:

$$R^3-Y-\overset{H}{\underset{O}{\overset{|}{C}}}-\overset{H}{\underset{N}{\overset{|}{C}}}-X-R^4 \quad \text{(I)}$$

wherein
Y is NH;
X is O or S(O)m;
m is 0 or an integer having a value of 1, or 2;
$R_3$ is optionally substituted triphenylmethyl;
$R_4$ is optionally substituted $C_{1-10}$ alkyl, $(CR_{10}R_{20})_nC(R_{10})=C(R_7)_2$, or $(CR_{10}R_{20})n-C\equiv C-R_5$;
n is an integer having a value of 1 to 4;
$R_{10}$ and $R_{20}$ are independently hydrogen or $C_{1-4}$ alkyl;
$R_5$ is hydrogen, alkyl, aryl, arylalkyl, heteroaryl, heteroarylalkyl, $C(O)_2R_6$, or $C(O)R_6$ wherein the alkyl, aryl, arylalkyl, heteroaryl, heteroarylalkyl moieties may be optionally substituted;
$R_6$ is $C_{1-10}$ alkyl, aryl, arylalkyl, heteroaryl, heteroarylalkyl, heterocyclic, or heterocyclicalkyl, all of which may be optionally substituted:
$R_7$ is independently hydrogen. $C_{1-10}$ alkyl, aryl, arylalkyl, heteroaryl. heteroarylalkyl, heterocyclic, or heterocyclicalkyl, all of which may be optionally substituted;
or a pharmaceutically acceptable salt thereof.

DETAILED DESCRIPTION OF THE INVENTION

The present invention is directed to a novel method of treating inflammatory disease in a mammal in need thereof by administering to said mammal an effective amount of a compound according to Formula (I). The compounds of Formula (I) selectively inhibit the CoA-IT enzyme. This will result in the treatment of inflammatory occurrences in mammals. Inflammatory states in mammals may include, but are not limited to, allergic and asthmatic manifestations, dermatological diseases, inflammatory diseases, collagen diseases, reperfusion injury and stroke. Treatment of both acute and chronic diseases are possible. Preferred diseases for treatment are arthritis, asthma, allergic rhinitis, inflammatory bowel disease (IBD), psoriasis, reperfusion injury and stroke. For the purposes herein, the compounds of Formula (I) are preferential and selective inhibitors of CoA-IT.

Suitably, in compounds of Formula (I), X is O or S(O)m; and m is 0 or an integer having a value of 1, or 2. Preferably m is 0 or 2.

Suitably, in compounds of Formula (I), $R_3$ is optionally substituted triphenylmethyl group. The phenyl rings may be independently substituted one to three times by halogen, such as fluorine, chlorine, bromine or iodine; hydroxy; hydroxy substituted $C_{1-10}$ alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; S(O)m aryl; amino, mono & di- $C_{1-10}$ alkyl substituted amino; $C_{1-10}$ alkyl; halosubstituted $C_{1-10}$ alkyl, such as $CF_3$; CHO, $C(O)C_{1-10}$ alkyl, C(O) aryl, $C(O)_2R_8$, wherein $R_8$ is $C_{1-10}$ alkyl, aryl, or arylalkyl; $C(O)NR_9R_{11}$; cyano; $S(O)_2 NR_9R_{11}$; $N(R_{10})C(O)R_6$; $N(R_{10})C(O) NR_9R_{11}$; $N(R_{10})C(O) OR_6$; or $N(R_{10})S(O)_2R_6$.

Suitably, $R_9$ and $R_{11}$ are independently hydrogen, $C_{1-10}$ alkyl, aryl, arylalkyl.

Suitably, $R_4$ is optionally substituted $C_{1-10}$ alkyl $(CR_{10}R_{20})_nC(R_{10})=C(R_7)_2$, or $(CR_{10}R_{20})n—C≡C—R_5$; wherein n is an integer having a value of 1 to 4. Preferably n is 1.

When $R_4$ is an optionally substituted $C_{1-10}$ alkyl, the alkyl moiety may be straight or branched, and may be substituted one or more times, independently by halogen, such as fluorine; hydroxy; $C_{1-10}$ alkoxy; S(O)m alkyl, wherein m is 0, 1 or 2; amino, mono & di-substituted amino, such as $NR_9R_{11}$ group; wherein $R_9$ and $R_{11}$ are as described above, or $R_9$ and $R_{11}$ together with the nitrogen to which they are attached cyclize to form a 5 to 7 membered ring which optionally includes an additional heteroatom selected from O/N/S; —$O(CR_{10}R_{20})_sO$— wherein s is an integer having a value of 2 to 4 and both oxygens are attached to the same carbon in $R_4$; —$S(CR_{10}R_{20})_sS$— wherein s is as previously defined and both sulfurs are attached to the same carbon in R4; cycloalkyl, or a cycloalkyl alkyl group; a halosubstituted $C_{1-4}$ alkyl, such as $CF_3$; an optionally substituted aryl, such as phenyl, or an optionally substituted arylalkyl, such as benzyl or phenethyl, heteroaryl, or heteroarylalkyl, wherein these aryl or heteoaryl moieties may also be substituted one to two times by halogen; hydroxy; hydroxy substituted alkyl; $C_{1-10}$ alkoxy; $S(O)_m$ alkyl; amino, mono & di-$C_{1-4}$ alkyl substituted amino, such as in the $NR_9R_{11}$ group (wherein $R_9$ and $R_{11}$ are as defined above); $C_{1-10}$ alkyl, or $CF_3$.

Preferably, $R_4$ is a $C_{1-4}$ alkyl, such as isobutyl, or an alkenyl, such as isobutenyl.

Suitably, $R_{10}$ and $R_{20}$ are independently hydrogen or $C_{1-4}$ alkyl.

Suitably, $R_5$ is hydrogen, $C_{1-10}$ alkyl, aryl, arylalkyl, heteroaryl, heteroarylalkyl, $C(O)_2R_6$, $C(O)R_6$. Preferably $R_5$ is hydrogen, $C(O)_2R_6$, or a heteroaryl ring, and preferably $R_6$ therein is a C 1-4 alkyl, such as methyl. If $R_5$ is a heteroaryl ring, it is preferably a 2-, 3,- or 4-pyridyl. The alkyl, aryl, arylalkyl, heteroaryl, and heteroarylalkyl may be optionally substituted as herein defined.

Suitably, $R_6$ is $C_{1-10}$ alkyl, aryl, arylalkyl, heteroaryl, heteroarylalkyl, heterocyclic, or heterocyclicalkyl. The aryl, arylalkyl, heteroaryl, heteroarylalkyl, heterocyclic, and heterocyclicalkyl moieties may be optionally substituted as herein defined.

Suitably, $R_7$ is independently hydrogen, $C_{1-10}$ alkyl, aryl, arylalkyl, heteroaryl, heteroarylalkyl, heterocyclic, or heterocyclicalkyl. The alkyl, aryl, arylalkyl, heteroaryl, heteroarylalkyl, heterocyclic, and heterocyclicalkyl moieties may be optionally substituted as herein defined.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid The following terms, as used herein, refer to:

"halo"—all halogens, that is chloro, fluoro, bromo and iodo;

"$C_{1-10}$ alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

"cycloalkyl" is used herein to mean cyclic radicals, preferably of 3 to 8 carbons, including but not limited to cyclopropyl, cyclopentyl, cyclohexyl, and the like;

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1 -butenyl, 2-butenyl and the like;

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, 0 or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole;

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine;

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate;

"sulfinyl"—the oxide S (O) of the corresponding sulfide, the term "thio" refers to the sulfide, and the term "sulfonyl" refers to the fully oxidized $S(O)_2$ moiety;

"aroyl"—a C(O)Ar, wherein Ar is as phenyl, naphthyl, or aryl alkyl derivative such as defined above, such group include but are note limited to benzyl and phenethyl;.

"alkanoyl"—a $C(O)C_{1-10}$ alkyl wherein the alkyl is as defined above.

"optionally substituted" unless specifically defined for a particular substituent group, shall mean such groups as halogen, such as fluorine, chlorine, bromine or iodine; hydroxy; hydroxy substituted $C_{1-10}$ alkyl; $C_{1-10}$ alkoxy, such as methoxy or ethoxy; S(O)m alkyl, wherein m is 0, 1 or 2, such as methyl thio, methylsulfinyl or methyl sulfonyl; amino, mono & di-substituted amino, such as in $NR_9R_{11}$ group; $C_{1-10}$ alkyl, cycloalkyl, or cycloalkyl alkyl group, such as methyl, ethyl, propyl, isopropyl, t-butyl, etc., cyclopropyl, or cyclopropyl methyl; halo-substituted $C_{1-10}$ alkyl, such as $CF_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; $S(O)_m$ alkyl; amino, mono & di-$C_{1-4}$ alkyl substituted amino, such as in the $NR_9R_{11}$ group; $C_{1-10}$ alkyl, or $CF_3$.

It is recognized that the compounds of the present invention may exist as stereoisomers, regioisomers, or diastereoisomers. These compounds may contain one or more asymmetric carbon atoms and may exist in racemic and optically active forms. All of these compounds are included within the scope of the present invention.

Another aspect of the present invention are the novel compounds of Formula (Ia) represented by the structure:

(Ia)

wherein
Y is NH;
X is O or S(O)m;
m is 0 or an integer having a value of 1, or 2;
$R_3$ is optionally substituted triphenylmethyl;
$R_4$ is optionally substituted $C_{1-10}$ alkyl, $(CR_{10}R_{20})_nC(R_{10})=C(R_7)_2$, or $(CR_{10}R_{20})n$—C≡C—$R_5$;
n is an integer having a value of 1 to 4;
$R_{10}$ and $R_{20}$ are independently hydrogen or $C_{1-4}$ alkyl;
$R_5$ is hydrogen, alkyl, aryl, arylalkyl, heteroaryl, heteroarylalkyl, $C(O)_2R_6$, or $C(O)R_6$ wherein the alkyl, aryl, arylalkyl, heteroaryl and heteroarylalkyl moieties may be optionally substituted;
$R_6$ is $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;
$R_7$ is independently hydrogen, $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, and heterocyclicalkyl moieties may be optionally substituted;
excluding 4-methoxy-3-(triphenylmethylamino)azetidin-2-one, 3-(triphenylmethylamino)-azetidin-2-one, 4-(isobutenyloxy)-3-(triphenylmethylamino)azetidin-2-one, 4-(methylsulfonyl)-3-(triphenylmethylamino)azetidin-2-one, and 4-(prop-2-ynyloxy)-3-(triphenylmethylamino)azetidin-2-one;
or a pharmaceutically acceptable salt thereof.

For compounds of Formula (Ia), the variables Y, X, n, m, $R_3$, $R_4$, $R_{10}$, $R_{20}$, $R_5$, $R_6$, and $R_7$ are as defined above for compounds of Formula (I).

Specifically exemplified compounds of Formula (I) are:
(3RS,4RS)-4-(Isobutoxy)-3-(triphenylmethylamino)azetidin-2-one
(3R,4R)-4-(Isobutoxy)-3-(triphenylmethylamino)azetidin-2-one
(3S ,4S)-4-(Isobutoxy)-3-(triphenylmethylamino)azetidin-2-one
(3R,4R)-4-(Isobutylthio)-3-(triphenylmethylamino)azetidin-2-one
(3R,4R)-4-(Isobutylsulfonyl)-3-(triphenylmethylamino)azetidin-2-one
(3S,4R)-4-(Isobutoxy)-3-(triphenylmethylamino)azetidin-2-one
(3S,4R)-4-(Propoxy)-3-(triphenylmethylamino)azetidin-2-one
(3S ,4S)-4-(Propoxy)-3-(triphenylmethylamino)azetidin-2-one
(3S,4R)-4-(Benzyloxy)-3-(triphenylmethylamino)azetidin-2-one
(3S,4S)-4-(Benzyloxy)-3-(triphenylmethylamino)azetidin-2-one
(3S,4R)-4-Methoxy-3-(triphenylmethylamino)azetidin-2-one
(3S,4R)-4-(Isobutenyloxy)-3-(triphenylmethylamino)azetidin-2-one
(3S,4R)-4-Octyloxy-3-(triphenylmethylamino)azetidin-2-one
(3S ,4R)-4-Phenoxy-3-(triphenylmethylamino)azetidin-2-one
(3S,4S)-4-Phenoxy-3-(triphenylmethylamino)azetidin-2-one
(3S,4R)-3-[[(4-Iodophenyl)diphenylmethyl]amino]-4-(isobutoxy)azetidin-2-one
(3S,4S)-4-[3-(Methoxycarbonyl)propoxy]-3-(triphenylmethylamino)azetidin-2-one
(3S,4R)-4-[[2-(3-Pyridylmethyl)-1 ,3-dithian-2-yl]methoxy]-3-(triphenylmethylamino)-azetidin-2-one
(3S,4S)-4-(Prop-2-ynyloxy)-3-(triphenylmethylamino)azetidin-2-one
Methyl 4-[(3S,4S)-2-oxo-3-(triphenylmethylamino)azetidin-4-yloxy]but-2-ynoate
Methyl 4-[(3S,4R)-2-oxo-3-(triphenylmethylamino)azetidin-4-yloxy]but-2-ynoate
(3S,4R)-4-[(2(5H)Furanon-4-yl)methoxy]-3-(triphenylmethylamino)azetidin-2-one
(S)-3-(Triphenylmethylamino)azetidin-2-one
(RS)-3-(Triphenylmethylamino)azetidin-2-one
(3R,4R)-4-(Methylsulfonyl)-3-(triphenylmethylamino)azetidin-2-one Compounds of formula (I) where 4-(X—$R^4$) is 4-(O—$R^4$) or 4-(S—$R^4$) can be prepared according to Scheme I from 1, where $R^3$ is defined as in formula (I) and Y is a suitable leaving group such as methylsulfonyl, acyloxy, or chloro. Compounds 1, where Y is methylsulfonyl, are obtained as described in J. Chem. Soc. Perkin I, 447, 1976 whose disclosure is incorporated herein by reference. The displacement of group Y in 1 with HO—$R^4$ or HS—$R^4$ may be carried out with a suitable catalyst such as zinc acetate in a suitable solvent such as toluene at a suitable temperature such at 90° C. Alternatively, with phenols, the displacement may be carried out in the presence of a suitable base, such as aqueous sodium hydroxide, in a suitable solvent such as acetone.

Compound 3 where 4-(X—$R^4$) is 4-(SO—$R^4$) and 4-(SO$_2$—$R^4$) and $R^3$, $R^4$ are defined as in formula (I), can be obtained by further oxidation of 2 where 4-(X—$R^4$) is 4-(S—$R^4$) with a suitable organic oxidizing agent such as m-chloroperbenzoic, peracetic acid, etc. in a suitable solvent such as dichloromethane, or by further oxidation with a suitable inorganic oxidizing agent such as sodium periodate or potassium permangante in a solvent such as water, acetone or acetic acid.

Scheme I

Alternatively, compounds of formula (I) may be prepared according to Scheme II from 4. Compound 4, wherein X is O—R⁴ or S—R⁴ and R⁴ is as defined in formula (I) and R¹ is hydrogen, can be prepared from 4-acetoxy or 4-benzoyloxy-azetidin-2-one as described in Synthetic Communications, 24, 131–135 (1994) whose disclosure is incorporated herein by reference. Treatment of 4, where R¹ is hydrogen, with a suitable silylating group such as tert-butyldimethylsilyl chloride and a suitable base such as triethylamine in a suitable solvent such as tetrahydrofuran gives 4 where R¹ is tert-butyldimethylsilyl. Treatment of 4, where R¹ is tert-butyldimethylsilyl, with a suitable base such as lithium diisopropylamide in a suitable solvent such as tetrahydrofuran at a suitable temperature such as –50° C., followed by addition to a solution of a suitable azidating reagent such as tosyl azide in a suitable solvent such as tetrahydrofuran, followed by treatment with trimethylsilyl chloride gives 5 where R¹ is tert-butyldimethylsilyl. Reduction of the azido group in 5, where R¹ is tert-butyldimethylsilyl, with a suitable reducing agent such as hydrogen sulfide in a suitable solvent such as dichloromethane containing a suitable base such as triethylamine gives 6 where R¹ is tert-butyldimethylsilyl. Treatment of 6, where R¹ is tert-butyldimethylsilyl, with a suitable alkylating agent R³Z, where R³ is as defined in formula (I) and Z is a suitable leaving group such as chloro, in a suitable solvent such as dimethylformamide containing a suitable base such as diisopropylethylamine, gives 2 where R¹ is tert-butyldimethylsilyl. Treatment of 2, where R¹ is tert-butyldimethylsilyl, with a suitable inorganic fluoride, such as tetrabutylammonium fluroride, in a suitable solvent such as tetrahydrofuran and acetic acid gives 2 where R¹ is hydrogen.

Scheme II

Alternatively, compounds II-5 may be prepared using [2+2] cycloaddition reactions, for example, by following the general procedures described in Cama et. al., Tetrahedron Letters, 4233, 1978, whose disclosure is incorporated herein by reference.

Synthetic Chemistry

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. ¹H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

EXAMPLE 1

Preparation of (3RS,4RS)-4-(Isobutoxy)-3-(triphenylmethylamino)azetidin-2-one a). 4-(Isobutoxy)azetidin-2-one A mixture of 4-(benzoyloxy)azetidin-2-one (15.2 g, 80 mmol) in toluene (150 mL) was treated with isobutanol (12 g, 0.16 mol), triethylamine (16 g, 0.16 mol) and palladium acetate (3.6 g, 16 mmol), stirred in an ice bath for several hours, allowed to warm to RT and stirred for 16 h. The mixture was filtered through Supercel, concentrated and the residue was chromatographed on silica gel eluted with 10–35% ethyl acetate:hexane. Fractions containing the product were combined, concentrated and rechromatographed on silica gel eluted with 10–25% ethyl acetate:hexane to give the title compound (4.9 g).

b). 1-tert-Butyldimethylsilyl-4-(isobutoxy)azetidin-2-one

A solution of 4-(isobutoxy)azetidin-2-one (4.8 g, 33 mmol) in tetrahydrofuran (50 mL) was stirred in an ice bath and treated with triethylamine (6.6 mL, 66 mmol) followed by dropwise addition of a solution of tert-butyldimethylsilyl chloride (6.5 g, 43 mmol) in tetrahydrofuran (15 mL). The mixture was stirred for 5 h in the cold and stored in the refrigerator for 64 h. The mixture was poured into cold water, extracted with ethyl acetate, and the combined organic phase was washed with brine, dried (magnesium sulfate), and concentrated. The residue was chromatographed on silica gel eluted with 10% ethyl acetate:hexane. Fractions containing the product were pooled and concentrated to give the title compound (6.6 g, 79%).

c). (3RS,4RS)-3-Azido-1-(tert-butyldimethylsilyl)-4-(isobutoxy)azetidin-2-one

A solution of N-(isopropyl)cyclohexylamine (1.5 g, 10 mmol) in tetrahydrofuran (18 mL) was cooled to −15° C. and 2 M butyllithium (48 mL, 10 mmol) was added dropwise. The reaction mixture was stirred for 40 min, the temperature was lowered to −70° C., and the mixture was treated dropwise over 10 min with a solution of 1-(tert-butyldimethylsilyl)-4-(isobutoxy)-azetidin-2-one (1.8 g, 7 mmol) in tetrahydrofuran (7 mL). The mixture was stirred for 1 h, transferred to a jacketed addition funnel maintained at −70° C., and added over 40 min to a solution of p-toluenesulfonyl azide (1.8 g, 9 mmol) in tetrahydrofuran (8 mL) containing hexamethylphosphoramide (2 mL) maintained at −70° C. The reaction was stirred for 1 h and at −50° C. for 4.5 h. The mixture was stirred at −28° C. for 16 h, and trimethylsilyl chloride (5 mL) was added and the mixture was stirred at RT for 45 min. The mixture was diluted with water and extracted with ethyl acetate. The combined organic phases were washed with brine, dried (magnesium sulfate) and concentrated. The residue was chromatographed on silica gel eluted with 10% ethyl acetate:hexane to give the title compound (0.6 g, 30%). MS(ES) m/e 299 [M+H]$^+$.

d). (3RS,4RS)-3-Amino-1-(tert-butyldimethylsilyl)-4-(isobutoxy)azetidin-2-one

A solution of (3RS,4RS)-3-azido-1-(tert-butyldimethylsilyl)-4-(isobutoxy)azetidin-2-one (0.2 g, 0.67 mmol) in dichloromethane (15 mL) containing triethylamine (0.07 g, 0.7 mmol) was cooled in an ice bath and hydrogen sulfide was bubbled through the solution gently for 10 min. The mixture was stirred in the cold for 4 h, concentrated, and then treated with dichloromethane and concentrated four times to give the title compound.

e). (3RS,4RS)-1-(tert-Butyldimethylsilyl)-4-(isobutoxy)-3-(triphenylmethylamino)azetidin-2-one A solution of (3RS,4RS)-3-amino-1-(tert-butyldimethylsilyl)-4-(isobutoxy)azetidin-2-one (0.2 g) was dissolved in dimethylformamide (8 mL), cooled in an ice bath, and treated with diisopropylethylamine (0.1 mL) followed by trityl chloride (167 mg, 0.6 mmol). The mixture was stirred for 18 h, diluted with water (40 mL) and extracted with ethyl acetate. The combined organic phase was dried (magnesium sulfate), concentrated, and the residue was chromatographed on silica gel eluted with 20% ethyl acetate:hexane to give the title compound. MS(ES) m/e 515 [M+H]$^+$.

f). (3RS,4RS)-4-(Isobutoxy)-3-(triphenylmethylamino)azetidin-2-one

A solution of (3RS,4RS)-1-(tert-butyldimethylsilyl)-4-(isobutoxy)-3-(triphenylmethylamino)azetidin-2-one (160 mg, 0.3 mmol) in tetrahydrofuran (4 mL) was cooled in an ice bath and treated with acetic acid (25 mg, 0.4 mmol) followed by dropwise addition of 1 M tetrabutylammonium fluoride (0.6 mL, 0.6 mmol). The mixture was stirred for 20 min and passed through silica gel (10 g) eluted with ethyl acetate. The eluate was concentrated and the residue was chromatographed on silica gel eluted with 20% ethyl acetate:hexane to give the title compound. MS(ES) m/e 423 [M+Na]$^+$.

EXAMPLE 2

Preparation of (3R,4R)- and (3S,4S)-4-(Isobutoxy)-3-(triphenylmethylamino)azetidin-2-one (3RS,4RS)-4-(Isobutoxy)-3-(triphenylmethylamino) azetidin-2-one was resolved by HPLC (Chiralcel OD, 21×250 mm, 10 mL/min, gradient, A:ethanol B:hexane, 0.5–2.5% A during 20 min, UV detection at 254 nm) to afford the title compounds:
(3R,4R)-4-(isobutoxy)-3-(triphenylmethylamino)azetidin-2-one, $t_R$ 35 min.
MS(ES) m/e 801 [2 M+H]$^+$, and
(3S,4S)-4-(isobutoxy)-3-(triphenylmethylamino)azetidin-2-one, $t_R$ 39.9 min.
MS(ES) m/e 801 [2 M+H]$^+$.

EXAMPLE 3

Preparation of (3R,4R)-4(Isobutylthio)-3-(triphenylmethylamino)azetidin-2-one

A solution of zinc acetate (0.7 g, 3 mmol) in toluene (15 mL) and 2-methyl-propanethiol (0.72 g, 8 mmol) was refluxed for 45 min in an apparatus equipped with a Dean-Stark trap to azeotrope water. (3R,4R)-4-(Methylsulfonyl)-3-(triphenylmethylamino)azetidin-2-one (1.5 g, 36 mmol) was added and the mixture was heated to 90° C. for 2 h. The mixture was concentrated and the residue was triturated with ethyl acetate and the insoluble material was removed by filtration. The filtrate was concentrated and the residue was chromatographed on silica gel eluted with 20% ethyl acetate:hexane. The fractions containing the product were combined, concentrated to give the title compound. MS(ES) m/e 417 [M+H]$^+$.

EXAMPLE 4

Preparation of (3R,4R)-4-(Isobutylsulfonyl)-3-(triphenylmethylamino)azetidin-2-one A solution of (3R,4R)-4-(isobutylthio)-3-(triphenylmethylamino)azetidin-2-one (50 mg, 0.12 mmol) in dichloromethane (2 mL) was cooled in an ice bath and treated with m-chloroperbenzoic acid (44 mg, 0.25 mmol). The mixture was stirred for 2.5 h in the cold and partitioned between 5% sodium carbonate (5 mL) and dichloromethane. The organic phase was washed with 5% sodium carbonate and with brine, dried (magnesium sulfate), filtered and concentrated. The residue was chromatographed on silica gel eluted with 20% ethyl acetate:hexane and fractions containing the product were pooled and concentrated to give the title compound (25 mg, 47%). MS(ES) m/e 447 [M−H]$^+$.

EXAMPLES 5–13

The following compound have been prepared using the procedure of Example 3, except substituting isobutanol, propanol, benzyl alcohol, methanol, isobutenol, or octanol for 2-methyl-propanethiol gave:

Example 5: (3S,4S)-4-(Isobutoxy)-3-(triphenylmethylamino)azetidin-2-one: MS(ES) m/e 801 [2 M+H]+;
Example 6: (3S,4R)-4-(Isobutoxy)-3-(triphenylmethylamino)azetidin-2-one: MS(ES) m/e 401 [M+H]+;
Example 7: (3S,4R)-4-(Propoxy)-3-(triphenylmethylamino)azetidin-2-one: MS(ES) m/e 387 [M+H]+;
Example 8: (3S,4S)-4(Propoxy)-3-(triphenylmethylamino)azetidin-2-one: MS(ES) m/e 773 [2M+H]+;
Example 9: (3S,4R)-4-(Benzyloxy)-3-(triphenylmethylamino)azetidin-2-one: MS(ES) m/e 435 [M+H]+;
Example 10: (3S,4S)-4 -(Benzyloxy)-3-(triphenylmethylamino)azetidin-2-one: MS(ES) m/e 435 [M+H]+;
Example 11: (3S,4R)-4-Methoxy-3-(triphenylmethylamino)azetidin-2-one: MS(ES) m/e 359 [M+H]+;
Example 12: (3S,4R)-4-(Isobutenyloxy)-3-(triphenylmethylamino)azetidin-2-one: MS(ES) m/e 399 [M+H]+;
Example 13: (3S,4R)-4-Octyloxy-3-(triphenylmethylamino)azetidin-2-one: MS(ES) m/e 457 [M+H]+;

EXAMPLES 14-15

Preparation of (3S,4R)-4-Phenoxy-3-(triphenylmethylamino)azetidin-2-and (3S,4S)-4-Phenoxy-3-(triphenylmethylamino)azetidin-2-one A solution of phenol (0.3 g, 3.2 mmol) in acetone (3 mL) was treated with 1 N sodium hydroxide (3.2 mL, 3.2 mmol), stirred 10 min and treated dropwise with a solution of (3R,4R)-4-methylsulfonyl-3-(triphenylmethylamino)azetidin-2-one (1.2 g, 3 mmol) in acetone (2 mL). The mixture was stirred for 1.5 h, partitioned between water and diethyl ether, and the combined organic phase was washed with brine, dried (magnesium sulfate), and concentrated. The residue was chromatographed on silica gel eluted with 20% ethyl acetate:hexane to give the title compounds:
(3S,4R)-4-phenoxy-3-(triphenylmethylamino)azetidin-2-one: MS(ES) m/e 443 [M+Na]+; 421 [M+H]+;
(3S,4S)-4-phenoxy-3-(triphenylmethylamino)azetidin-2-one: MS(ES) m/e 841 [2 M+H]+; 419 [M-H]−.

EXAMPLE 16

Preparation of (3S,4R)-3-[[(4-Iodophenyl)diphenylmethyl]amino]4-(isobutoxy)azetidin-2-one a). (3S,4R)-3-Amino4(isobutoxy)azetidin-2-one para-toluenesulfonate A solution of para-toluenesulfonic acid hydrate (190 mg) in acetone (20 mL) was added to a solution of (3S,4R)-4-isobutoxy-3-(triphenylmethylamino)azetidin-2-one (400 mg, 1 mmol) in acetone (20 mL), stirred for 1 h, and concentrated. The residue was triturated with diethyl ether and the resulting solid isolated by filtration to give the title compound (180 mg, 55%).

b). (3S,4R)-3-[[(4-Iodophenyl)diphenylmethyl]amino]-4-(isobutoxy)azetidin-2-one

A solution of (3S,4R)-3-amino-4-(isobutoxy)azetidin-2-one para-toluenesulfonate (180 mg, 0.54 mmol) in acetone (8 mL) containing diisopropylethylamine ( 1.1 mmol) was treated with a solution of (4-iodophenyl)diphenylmethyl chloride (218 mg, 0.54 mmol), prepared as described by Tschitschibabin, Chem. Ber. 44, 450 (191 1), in acetone (98 mL). The solution was stirred for 6 h and partitioned between water and dichloromethane. The combined organic phases were dried (magnesium sulfate), concentrated, and the residue was chromatographed on silica gel eluted with 15% ethyl acetate:hexane to give the title compound (190 mg, 67%). MS(ES) m/e 527 [M+H]+.

EXAMPLE 17

Preparation of (3S,4S)-4-[3-(Methoxycarbonyl)propoxy]-3-(triphenylmethylamino)azetidin-2-one a). (3S,4S)-3-Amino-4-[3-(methoxycarbonyl)propoxy]azetidin-2-one A solution of methyl 4-[(3S,4S)-2-oxo-3-(triphenylmethylamino)azetidin-4-yloxy]but-2-ynoate (75 mg, 0.17 mmol) in absolute ethanol (6 mL) was treated with 10% palladium-on-carbon (35 mg) and stirred under hydrogen overnight. The catalyst was removed by filtration and the filtrate concentrated. The residual oil was purified on by preparative thin layer chromatography (Whatman, silica gel 60A, 20×20 cm, 1000 um, 20% ethyl acetate:hexane). The origin band contained the title compound (30 mg). MS(ES) m/e 203.0 [M+H].

b). (3S,4S)-4-[3-(Methoxycarbonyl)propoxy]-3-(triphenylmethylamino)azetidin-2-one
(3S,4S)-3-Amino-4-[3-(methoxycarbonyl)propoxy]azetidin-2-one (30 mg, 0.148 mmol) was dissolved in dry dichloromethane (2 mL) and treated with triphenylmethyl chloride (41 mg, 0.148 mmol) followed by diisopropylethylamine (19 mg, 0.148 mmol). The solution was stirred at RT under argon for 5 h, diluted with water and extracted with dichloromethane. The organic phases were combined, washed with water and brine, dried (magnesium sulfate), filtered, and concentrated. The residue was purified by preparative thin layer chromatography (Whatman, silica gel 60A, 20×20 cm, 1000 um, 40% ethyl acetate:hexane) to give the title compound (7 mg). MS(ES) m/e 445.2 [M+H].

EXAMPLES 18–21

The following compounds were prepared using the general procedure of Example 3, except substituting:
Examples 18 and 19: methyl 4-hydroxy-2-butynoate (Zh. Obshch. Khim. 66, 106, 1996),
Example 20: 4-hydroxymethyl-2(5 H)-furanone, (J. Chem. Res., Synop. 222, 1986),
or
Example 21: 2-(3-pyridylmethyl)-1,3-dithianyl-2-methanol for 2-methyl-propanethiol used therein.
Preparation of

EXAMPLE 18:

Methyl 4-[(3S,4S)-2-oxo-3-(triphenylmethylamino)azetidin-4-yloxy]but-2-ynoate
Methyl 4-[(3S,4S)-2-oxo-3-(triphenylmethylamino)azetidin-4-yloxy]but-2-ynoate:
$^1$H NMR(270 MHz, CDCl$_3$) δ 3.54 (d, J=17 Hz, 1 H), 3.77 (s, 3 H), 3.83 (d, J=17 Hz, 1 H), 4.08 (s, 1 H), 4.11 (d, J=1.1 Hz, 1 H), 6.39 (s, 1 H), 7.19–7.53 (m, 15 H); IR(CHCl$_3$) 3330, 2240, 1770, 1718, 1477, 1445, 1434, 1260, 1194, 1166, 940, 759, 706 cm$^{-1}$.

EXAMPLE 19:

Methyl 4-[(3S,4R)-2-oxo-3-(triphenylmethylamino)azetidin-4-yloxy]but-2-ynoate
Methyl 4-[(3S,4R)-2-oxo-3-(triphenylmethylamino)azetidin-4-yloxy]but-2-ynoate:
$^1$H NMR(60 MHz, CDCl$_3$)δ 2.9 (d, J=9 Hz, 1 H), 3.70 (s, 3 H), 3.60 (d, J=17 Hz, 1H), 3.93 (d, J=17 Hz, 1 H), 4.0–4.3

(m, 2 H), 6.8 (s, 1 H), 7.2–7.8 (m, 15 H); IR(CHCl$_3$) 3350, 1775, 1715 cm$^{-1}$.

EXAMPLE 20:

(3S,4R)-4-[(2(5 H)Furanon-4-yl)methoxy]-3-(triphenylmethylamino)azetidin-2-one
(3S,4R)-4-[(2(5 H)furanon4-yl)methoxy]-3-(triphenylmethylamino)azetidin-2-one:
$^1$H NMR(60 MHz, CDCl$_3$) δ 2.8 (d, J=9 Hz, 1 H), 3.9 (m, 2 H), 4.2 (m, 2 H), 4.53 (m, 2 H), 5.87 (m, 1 H), 7.0–8.7 (m, 17 H); IR(CHCl$_3$) 1785, 1755, 1650 cm$^{-1}$.

EXAMPLE 21:

(3S,4R)-4[[2-(3-Pyridylmethyl)- 1.3-dithian-2-yl]methoxy]-3-(triphenylmethylamino)azetidin-2-one
(3S,4R)-4-[[2-(3-pyridylmethyl)-1,3-dithian-2-yl]methoxy]-3-(triphenylmethylamino)azetidin-2-one:
IR(CHCl$_3$) 3370, 1775 cm$^{-1}$.
Using analagous procedures to those indicated above, or as indicated, the following compounds have been syntheized:

EXAMPLE 22:

(3S,4S)-4-(Prop-2-ynyloxy)-3-(triphenylmethylamino)azetidin-2-one: J. Chem. Soc. Perkin Trans. I 2268, 1979;

EXAMPLE 23:

(3R,4R)-4-(Methylsulfonyl)-3-(triphenylmethylamino)azetidin-2-one, J. Chem. Soc. Perkin Trans. I 2268, 1979;

EXAMPLE 24:

(3S,4R)-4-(Isobutenyloxy)-3-(triphenylmethylamino)azetidin-2-one, J. Chem. Soc. Perkin Trans. I 2268, 1979;

EXAMPLE 25:

(S)-3-(Triphenylmethylamino)azetidin-2-one: Tetr. Letters 30, 3219, 1989.

EXAMPLE 26:

Using analagous procedures to those noted therein, the racemic mixture of (RS)-3-(Triphenylmethylamino)azetidin-2-one may be produced.

Methods of Treatment

The compounds of Formula (I) or pharmaceutically acceptable salts thereof can be used in the manufacture of a medicament for the prophylactic or therapeutic treatment of an inflammatory disease state in a mammal, preferably a human.

Inhibition of COA-IT and the simultaneous reduction of PAF, free arachidonic acid and eicosanoid release from inflammatory cells according to this invention is of therapeutic benefit in a broad range of diseases or disorders. The invention herein is therefore useful to treat such disease states both in humans and in other mammals.

Inhibition of CoA-IT by the compounds of Formula (I) is an effective means for simultaneously reducing PAF, free arachidonic acid and eicosanoids produced in inflammatory cells. The therapeutic utility of blocking lipid mediator generation has been recognized for many years. For example, inhibitors of cyclooxygenase, such as aspirin, indomethacin, acetaminophen and ibuprofen, have demonstrated broad therapeutic utilities. CoA-IT inhibitors inhibit cyclooxygenase products. Another class of inhibitors which are used in a broad range of inflammatory disorders are the corticosteroids. Corticosteroids act in a variety of ways, e.g. to induce inflammatory cells to produce proteins which inhibit free arachidonic acid release or to down regulate PLA$_2$ mRNA formation. Both 14 kDa PLA2 inhibitors and CoA-IT inhibitors block the release of free arachidonic acid. Inhibitors of 5-lipoxygenase block the production of leukotrienes and leukotriene antagonists prevent the bioactions of leukotrienes. Recent studies indicate that both will have broad therapeutic utilities. Both 14 kDa PLA2 inhibitors and CoA-IT inhibitors block the production of leukotrienes. Inhibitors of phospholipase A$_2$ block the release of free arachidonic acid and the formation of lyso PAF (the immediate precursor of PAF). PLA$_2$ inhibitors are recognized to have broad therapeutic utilities. It does not, however, follow that the disease states noted above must in fact be caused by altered CoA-IT activity. Thus, the disease state itself may not be directly mediated by CoA-IT activity. It only follows that CoA-IT activity is required for the continued expression of symptoms of the disease state and that CoA-IT inhibitors will be beneficial against the symptoms of these disease states.

Recognition that CoA-IT inhibitors reduce PAF production has a number of therapeutic implications. PAF itself has been implicated as being involved in a number of medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock.

Intravenous infusion of PAF at doses of 20–200 pmol kg<-1>min<-1> into rats has been reported to result in the formation of extensive haemorrhagic erosions in the gastric mucosa. Thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role is the disease of psoriasis. And finally, increasing evidence supports a potential patho-physiological role for PAF in cardiovascular disease. Thus recent studies in angina patients show PAF is released during atrial pacing. Intracoronary injection of PAF in pigs induces a prolonged decrease in coronary flow and, in guines pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke. Thus the compounds of the invention, by virtue of their ability to antagonise CoA-IT thus block the production of PAF, free arachidonic acid and its metabolites, are likely to be of value in the treatment of any of the above conditions.

Treatment of disease states caused by these lipid inflammatory mediators i.e., arachidonate, eicosanoids and PAF, include certain cardiovascular disorders such as but not limited to, myocardial infarction, stroke, circulatory shock, or hypotension, ischemia, reperfusion injury; inflammatory diseases such as, but not limited to, arthritis, inflammatory bowel disease, Crohn's disease, or ulcerative colitis; respiratory diseases such as but not limited to, asthma, or adult respiratory distress syndrome; analphylaxis, shock, such as but not limited to endotoxic shock; topical disesases, such as but not limited to actinic keratosis, psoriasis, or contact dermatitis; or pyresis.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. Such pharmaceutically acceptable carriers or diluents and methods of making are well known to those of skill in the art, and reference can be found in such texts as Remington's Pharmaceutical Sciences, 18th Ed., Alfonso R. Genarao, Ed., 1990, Mack Publishing Co. and the Handbook of Pharmaceutical Excipents, APhA Publications, 1986.

The compounds of formula (I) may also be administered in conventional dosages in combination with known second therapeutically active compounds, such as steroids or NSAID's for instance. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the Formula (I) or a pharmaceutically acceptable salt thereof calculated as the free base, the compound being administered from 1 to 4 times per day.

The choice of form for administration, as well as effective dosages, will vary depending, inter alia, on the condition being treated. The choice of mode of administration and dosage is within the skill of the art.

Biological Methods:

To determine activity of the compounds of Formula (I) various cellular assays can be used to determine in vitro activity. Additionally, various classical in vivo acute inflammatory models which have some aspect of their etilogy to elevated eicosanoid levels can be employed, such as the paw edema model, mouse zymosan peritonitis, reverse Arthus pleurisy or various skin inflammation assays which are described in Lewis et al., Experimental Models of Inflammation, in the *Handbook of Inflammation*, Vol. 5, Bonta Ed., Elsevier Science Publishers, N.Y. (1985) whose disclosure is herein incorporated by reference. The TPA induced ear edema model (mouse) is described herein as well. These classical models of inflammation will reflect the drug's ability to alter an inflammatory response but cannot address the specificity of drug action. These models have been traditionally designed as non steriod antiinflammatory drug sensitive pharmacological screens and it is important to utilize models which can differentiate PLA2 and CoA-IT inhibitors from NSAIDS.

Cell-free and Cellular Assessment of Inhibitors

Described herein is an in vitro assay for CoA-IT enzyme activity. A cellular assay for PAF production is also described herein.

Inflammatory Responses in vivo

The ability of compounds that inhibit CoA-IT to affect in vivo inflammatory responses may be assessed. Inflammatory responses are induced in the mouse ear by the topical application of a pro-inflammatory agent, such as 12-O-tetradecanoyl-phorbol 13-acetate. This produces an edematous response, as measured by increases in ear thickness, as well as increased inflammatory cellular infiltrate, as measured by increases in myeloperoxidase activity (as described in the methods). To further validate the mechanism of action inflammation induced by the direct adminstration of arachidonic acid can be used. In this case compounds altering arachidonic acid mobilization or liberation should be with our effect.

In Vitro Assays

Assay: CoA-IT Activity

The following is a method to measure CoA-IT activity and the effects of compounds on CoA-IT activity. The assay is based upon mixing cellular material containing CoA-IT activity with a stable lyso phospholipid such as 1-alkyl-2-acyl-GPC and measuring the production of phospholipid product such as 1-alkyl-2-acyl-GPC occurring in the absence of added CoA or CoA-fatty acids.

Cell Preparation

Any inflammatory cell that contains high levels of COA-IT activity can be used, such as neutrophils, macrophages or cell lines such as U937 cells. U937 cells were obtained from American Type Culture Collection and grown in RPMI-1640 media (Gibco, Grand Island, N.Y.) supplemented with 10% fetal bovine serum (Hyclone, Logan, Utah) at 37° C., 5% $CO_2$. Cells were grown without differentiation (basal state) by any agent, such as dimethyl sulfoxide. As used herein, "inflammatory cells" include, but are not limited to neutrophils, macrophages, monocytes, lymphocytes, eosinophils, basophils, and mast cells.

Microsomal preparation

Microsomes were prepared using standard techniques. In this case, cells were washed with a buffer of 250 mM sucrose, 10 mM Tris, 1 mM EGTA, 1 mM $MgCl_2$, pH 7.4 and ruptured by $N_2$ cavitation (750 psi, 10 minutes). The ruptured cells were centrifuged 1000×g, 5 minutes. The resulting supernatant was centrifuged at 20,000×g, ~20 minutes. Microsomes were prepared from this supernatant by centrifugation at 100,000×g, 60 minutes. The resulting pellet was washed once with assay buffer (150 mM NaCl, 10 mM $Na_2KPO_4$, 1 mM EGTA, pH 7.4), recentrifuged and the pellet resuspended in assay buffer (4–20 mg protein/ml) and was stored at −80° C. until assayed.

CoA-IT activity

CoA-IT activity was measured in 1.5 ml centrifuge tubes in a total volume of 100 ul. Microsomes were diluted in assay buffer to the desired protein concentration (6–20 ug/tube). The reaction was initiated by addition of [$^3$H]1-alkyl-2-lyso-sn-glycero-3-phosphocholine (GPC) (~0.1 uCi/tube) and 1 $\mu$M final cold 1-alkyl-2-lyso-GPC in assay buffer with 0.25 mg/ml fatty acid-poor bovine serum albumin (BSA) (Calbiochem, La Jolla, Calif.). [$^3$H]1-alkyl-2-lyso-GPC, approximately 50 Ci/mmol, was from NEN-Dupont (Boston, Mass.) and cold 1-alkyl-2-lyso-GPC was from Biomol (Plymouth Meeting, Pa.). Microsomes were pretreated with desired agents for the desired time (10 minutes) before the addition of [$^3$H]1-alkyl-2-lyso-GPC. The reaction was run for the desired time (10 minutes) at 37° C. The reaction was stopped and the lipids extracted by addition of 100 ul of chloroform:methanol (1:2, v/v) followed by 100 ul of chloroform and 100 ul of 1 M KCl. The samples were vortexed and centrifuged at high speed in a microfuge for 2–3 minutes. An aliquot of the chloroform-extracted materials were separated, usually by TLC in chloroform/methanol/acetic acid/water (50:25:8:4, v/v), visualized by radioscanning (Bioscan) and the product, [$^3$H]1-alkyl-2-acyl-GPC, was scraped and quantified by liquid scintillation spectroscopy. With this TLC system, the synthetic standards of 1-alkyl-2-lyso-GPC and 1-alkyl-2-acyl-GPC were well separated, with Rf values of approximately 0.25 and 0.65, respectively. Other methods can be used to separate substrate from product, including but not limited to column chromatography, affinity chromatography and post reaction derivitization.

Protein concentration were assessed using the protein assay reagents from Bio-Rad (Richmond, Calif.).

Results

A variety of compounds have been tested in this assay to determine its selectivity and inability to detect trivial, non-selective inhibitors. Inhibitors of 5-lipoxygenase (5-LO) and cyclooxygenase (CO), such as indomethicin, naproxen, 6-(4'-fluorophenyl)-5-(4-pyridyl)-2,3-dihydroimidzo-[2,1-b]thiazole and 6-(4'-fluorophenyl)-5-(4-pyridyl)2,3-dihydroimidzo-[2,1-b]thiazole-dioxide had no effect on CoA-IT activity at concentrations up to 100 $\mu$M. The antioxidant BHT also has no effect at concentrations up to 100 $\mu$M. Compounds which complex with phospholipids and inhibit $PLA_2$ activity, such as quinacrine and aristolochic acid have no effect on CoA-IT activity at concentrations up to 500 $\mu$M. Doxepine, a compound reported to inhibit PAF release did not inhibit CoA-IT at concentrations up to 100 $\mu$M. Sodium diclofenac, reported to decrease leukotriene production by altering arachidonic acid metabolism, had no effect on CoA-IT activity at concentrations up to 500 µM. These results show that the assay for CoA-IT activity is sensitive and selective.

Figure 1:
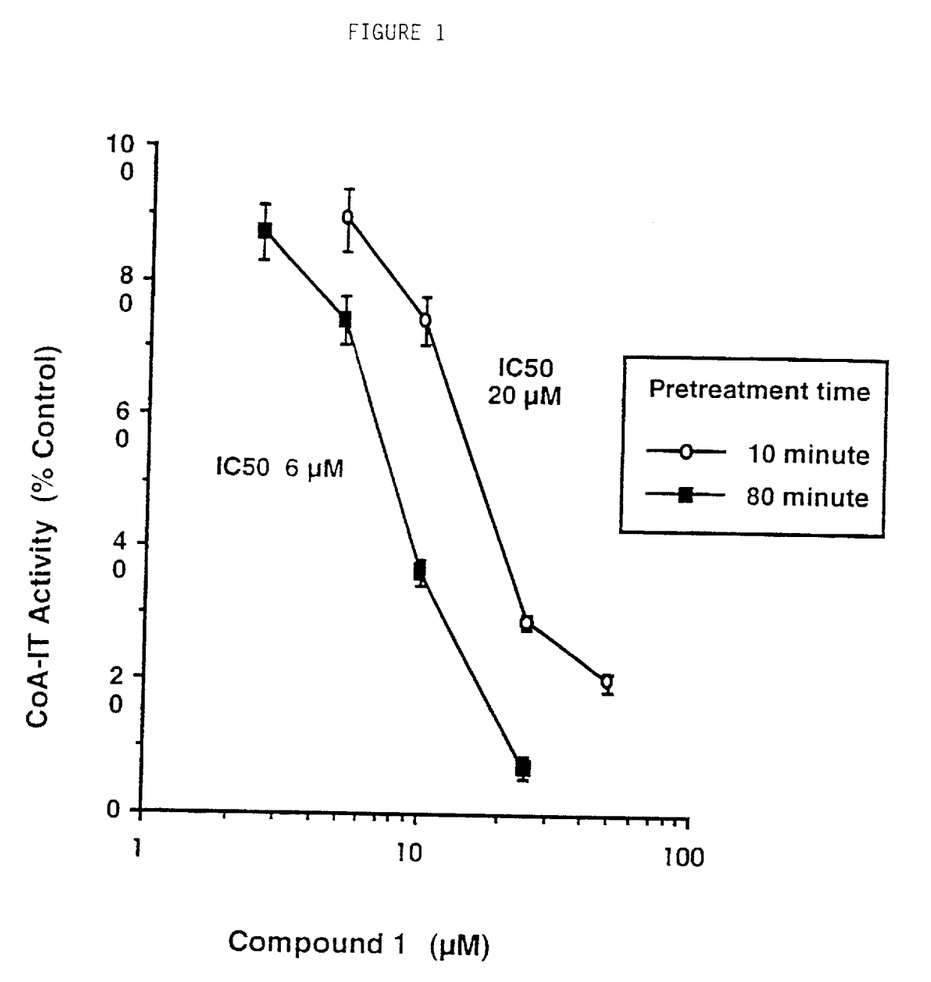
FIG. 1 demonstrates the time dependent inhibition of CoA-IT by (3S,4R)-4-(isobutenyloxy)-3-(triphenylmethylamino) azetidin-2-one.

FIG. 1 demonstrates the inhibition of CoA-IT activity in a time dependent manner using a representative compound of Formula (I), Example 24, (3S,4R)-4-(isobutenyloxy)-3-(triphenylmethylamino)azetidin-2-one.

Other representative compounds of Formula (I) which inhibited CoA-IT activity, as a time-dependent inhibitor, in the microsomal CoA-IT assay described above [generally at an $IC_{50}$ of <50 µM or less, at a 10 min preincubation time] are:

(3RS,4RS)-4-(Isobutoxy)-3-(triphenylmethylamino) azetidin-2-one
(3R,4R)-4-(Isobutoxy)-3-(triphenylmethylamino)azetidin-2-one
(3S,4S)-4-(Isobutoxy)-3-(triphenylmethylamino)azetidin-2-one
(3R,4R)-4-(Isobutylthio)-3-(triphenylmethylamino) azetidin-2-one
(3R,4R)-4-(Isobutylsulfony)-3-(triphenylmethylamino) azetidin-2-one
(3S,4R)-4-(Isobutoxy)-3-(triphenylmethylamino)azetidin-2-one
(3S,4R)-4-(Propoxy)-3-(triphenylmethylamino)azetidin-2-one
(3S,4S)-4-(Propoxy)-3-(triphenylmethylamino)azetidin-2-one
(3S,4R)-4-(Benzyloxy)-3-(triphenylmethylamino)azetidin-2-one
(3S,4S)-4-(Benzyloxy)-3-(triphenylmethylamino)azetidin-2-one
(3S,4R)-4-Methoxy-3-(triphenylmethylamino)azetidin-2-one
(3S,4R)-4-(Isobutenyloxy)-3-(triphenylmethylamino) azetidin-2-one
(3S,4R)-4-Octyloxy-3-(triphenylmethylamino)azetidin-2-one
(3S,4R)-4-Phenoxy-3-(triphenylmethylamino)azetidin-2-one
(3S,4S)-4-Phenoxy-3-(triphenylmethylamino)azetidin-2-one
(3S,4R)-3-[[(4-Iodophenyl)diphenylmethyl]amino]-4-(isobutoxy)azetidin-2-one
(3S,4R)-4-[[2-(Pyrid-3-yl)-1,3-dithian-2-yl]methoxy]-3-(triphenylmethylamino)azetidin-2-one
(3S,4S)-4-(Prop-2-ynyloxy)-3-(triphenylmethylamino) azetidin-2-one
Methyl 4-[(3S,4S)-2-oxo-3-(triphenylmethylamino) azetidin4-yloxy]but-2-ynoate
Methyl 4-[(3S,4R)-2-oxo-3-(triphenylmethylamino) azetidin-4-yloxy]but-2-ynoate
(3S,4R)-4-[(2(5 H)Furanon-4-yl)methoxy]-3-(triphenylmethylamino)azetidin-2-one
(S)-3-(Triphenylmethylamino)azetidin-2-one
(RS)-3-(Triphenylmethylamino)azetidin-2-one
(3S,4S)-4-[3-(Methoxycarbonyl)propoxy]-3-(triphenylmethylamino)azetidin-2-one
(3R,4R)-4-(Methylsulfonyl)-3-(triphenylmethylamino) azetidin-2-one.

The following compound was found active at either increased uM or longer pretreatment time:

(3S,4S)-4-[3-(Methoxycarbonyl)propoxy]-3-(triphenylmethylamino)azetidin-2-one
Assay Platelet-activating Factor (PAF)
Preparation of Human Neutrophils Human neutrophils are obtained in the laboratory using three different methods. One method uses leukophoresis packs from normal humans and neutrophils are isolated using the histopaque- 1077 technique. The blood is centrifuged at 300×g for 10 minutes. The cell pellets are resuspended in PBS composed of 137 mM NaCl, 8.8 mM $Na_2HPO_4$, 1.5 mM $KH_2PO_4$, 2.7 mM KCl (Dulbecco's Gibco Laboratories, Long Island, N.Y.) and layered over histopaque-1077 (Sigma, St. Louis, Mo.). The pellets are collected after centrifugation (300×g for 30 minutes) and washed once in PBS. The cell pellets are exposed briefly to deionized water to lyse any erythrocytes. The remaining cells are collected by centrifugation, suspended in PBS, counted and identified after cytospinning and staining. The final leukocyte preparation will be of greater than 95% purity and viability.

The second method isolates human neutrophils from fresh heparinized normal blood using the Histopaque-1077 technique. The blood is layered over Histopaque-1077 (Sigma, St. Louis Mo.) and centrifuged at 400×g for 30 minutes. The cell pellets are resuspended in 35 ml of PBS and 12 ml of 6% Dextran, followed by Dextran sedimentation at room temperature for 45 minutes. The upper layer is collected and further centrifugated for 10 minutes at 1000 rpm. The cell pellets are exposed briefly to deionized water to lyse erythrocytes. The remaining cells are collected by centrifugation, suspended in PBS, counted and identified after cytospinning and staining. The final leukocyte preparation will be of greater than 95% purity and viability.

The third method isolates human neutrophils from freshly drawn heparinized normal blood using the Percoll technique. The blood is first treated with 6% Dextran at room temperature for a 1 hour sedmination. The upper layers of plasma are collected and centrifuged at 400×g for 10 minutes. The cell pellets are resuspended in Percoll 1.070 g/ml supplemented with 5% fetal bovine serumand layered on discontinuous gradients (1.080, 1.085, 1.090,1.095 g/ml) followed by centrifugation at 400×g for 45 minutes. The neutrophils are collected from interfaces of 1;080 and 1.085 and the 1.085 and 1.090 Percoll densities, followed by a centrifugation at 400×g for 45 minutes. The neutrophils are suspended in PBS, counted and identified after cytospinning and staining. The final leukocyte preparation will be of greater than 95% purity and viability.

There should be no difference noted in the response of the neutrophils nor in the effects of test compounds in neutrophils isolated by the three different techniques.

Treatment of Human Neutrophils

Neutrophils were suspended in PBS at concentrations of 5 to 20×10⁶ cells per ml. Cells were added to test tubes and treated with the desired compounds for 5 to 10 minutes, then challenged with calcium ionophore A23187, 2 µM and 20–30 µCi of [$^3$H] acetic acid (NEN-Dupont, Boston, Mass.), or the vehicle of PBS with 0.25–1 mg/ml. After 5 to 20 minutes, the reactions were terminated by addition of an equal volume of chloroform:methanol (1:2, v/v) to the samples and the lipids were extracted by addition of equal volumes of chloroform and distilled water. The samples were vortexed and centrifuged at high speed and the chloroform layer removed to a clean tube.

Assay for PAF

The chloroform from each tube was evaporated to dryness and the material suspended in a small volume of chloroform or chloroform:methanol (25–100 µl) and the total material spotted on a Silica TLC plate. The plates were developed in chloroform/methanol/acetic acid/water (50:25:8:4, v/v) visualized by radioscanning (Bioscan) and the product,

[³H]PAF, was scraped and quantified by liquid scintillation spectroscopy. With this TLC system, the Rf value for a synthetic standard of PAF is approximately 0.33.

Figure 2:
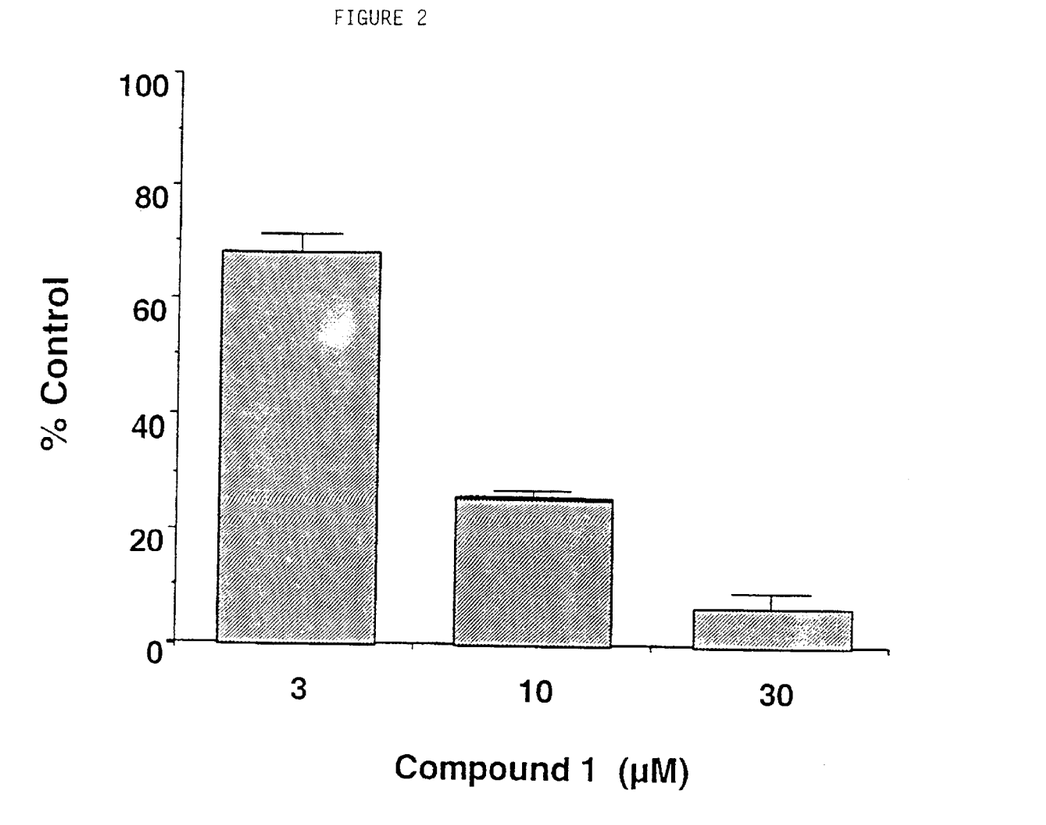
FIG. 2 demonstrates inhibition of PAF production in neutrophils by (3S,4R)-4-(isobutenyloxy)-3-(triphenylmethylamino)azetidin-2-one.

FIG. 2, demonstrates that a representative compound of Formula 1, Example 24 (3S,4R)-4-(Isobutenyloxy)-3-(triphenylmethylamino)azetidin-2-one blocks PAF production in neutrophils.

Assay: Measurement of Stimulated Eicosanoid Release by Human Monocytes.

Human Monocyte Isolation. Leukocyte-rich leukopaks obtained from Biological Specialties (Lansdale, Pa.) were collected from male volunteers who were not taking anti-inflammatory drugs. Leukopaks were centrifuged (90×g for 15 min) twice to remove the platelet-rich plasma. The cell pellet was washed by centrifugation and resuspended in HBSS without $Ca^{2+}$ or $Mg^{2+}$. Histopaque 1077 was layered under the cell suspension and centrifuged at 400×g for 30 min to obtain the buffy coat. The interfacial buffy coat, containing monocytes and lymphocytes, was removed and saved. The buffy coat was washed twice with HBSS without $Ca^{2+}$ or $Mg^{2+}$ by centrifugation. The cell pellet ($4-6\times10^8$ cells/30mls) was resuspended in iso-osmotic media (RPMI-1640, 10% heat inactivated fetal bovine serum (FBS), 0.2 mM L-glutamine, 2.5 mM HEPES) and layered over an equal volume of 46% Percol mixture (10X PBS/Percol; 9.25/0.75) and 54% iso-osmotic media and centrifuged for 30 min at 1000×g (Marshall and Roshak. Biochem. Cell Biol. 71: 331–339, 1993). The monocyte population located at the interface of the Percoll gradient was removed and washed twice in HBSS without $Ca^{2+}$ or $Mg^{2+}$. This resulted in a greater than 85–90% pure monocyte population as assessed by differential staining.

Measurement of Stimuli-Induced Eicosanoid Release. Monocytes ($5\times10^6$/ml) were incubated as a suspension in serum-free RPMI-1640 medium containing the vehicle DMSO (<1%) or drug for 30 min at 27° C. after which vehicle or stimuli was added for the indicated time. The stimulating agent is solubilized in DMSO and appropriate vehicle controls were included in all experiments. The amount of stimuli was chosen from the linear portion of a concentration versus product curve usually representing 60–80% maximal stimulation over the indicated incubation time at 37° C. (A23187, 1 $\mu$M. 15 min). The reaction was terminated by reduction of pH through addition of citric acid and centrifugation (10 min, 400×g. 4° C.). Cell viability was monitored before and after experiments using trypan blue exclusion. The cell-free media was decanted and stored al. −70° C. until analyzed. Prostaglandin $E_2$ and $LTC_4$ were directly measured in cell-free media using enzyme immunoassay (EIA) kits purchased from Caymen Chemical Co. (Ann Arbor, Mich.). Sample or standard dilutions were made with appropriate media and analyzed in triplicate. Results were obtained by extrapolation from a standard curve prepared in the media and expressed as pg or ng/ml of sample.

Figure 3:
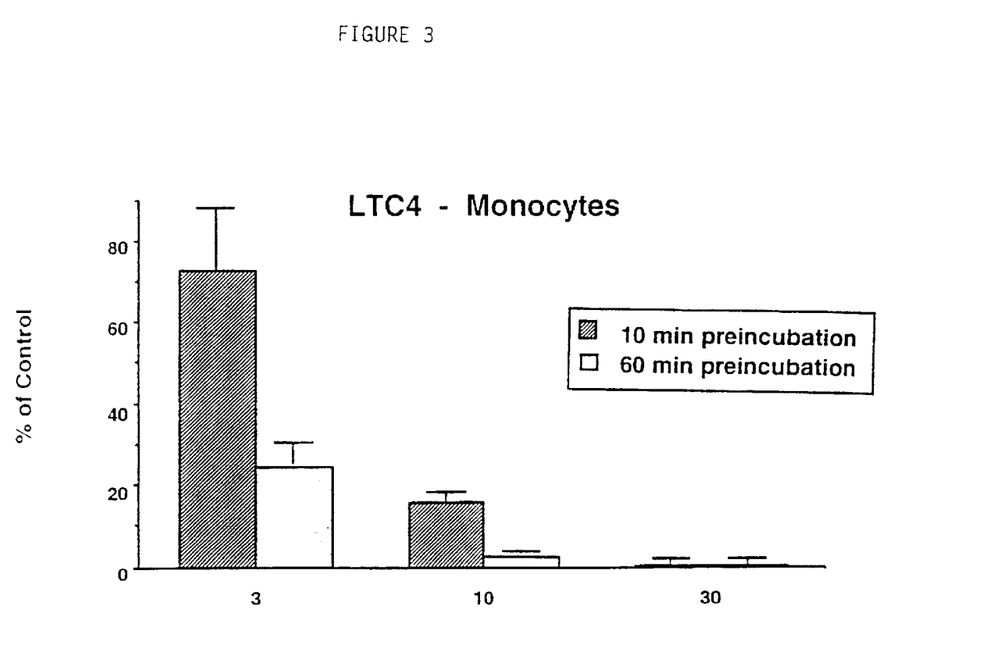
FIG. 3 demonstrates inhibition of $LTC_4$ production in monocytes by (3S,4R)-4-(isobutenyloxy)-3-(triphenylmethylamino)azetidin-2-one.
Figure 4:
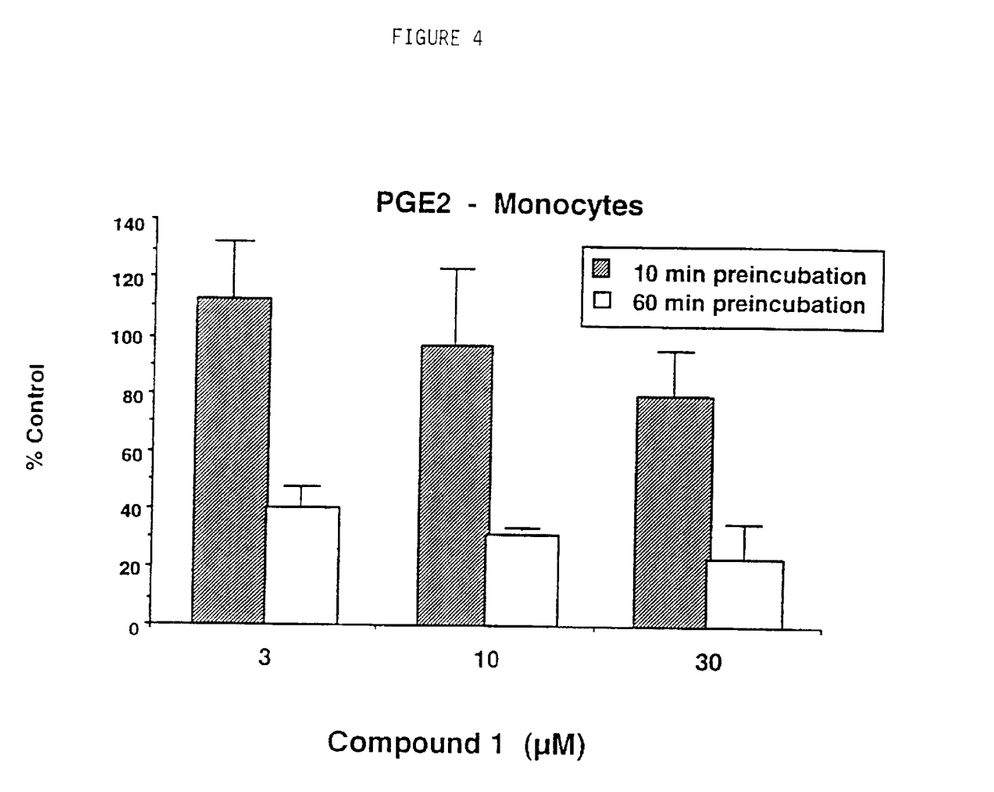
FIG. 4 demonstrates inhibition of $PGE_2$ production in monocytes by (3S,4R)-4-(isobutenyloxy)-3-(triphenylmethylamino)azetidin-2-one.

FIGS. 3 and 4 demonstrate that a representative compound of Formula (I), (3S,4R)-4-(isobutenyloxy)-3-(triphenylmethylamino)azetidin-2-one. Example 24 demonstrated positive activity in this assay. These Figures shows that this compound through its CoA-IT inhibition blocked the production of leukotriene and prostaglandin, and that such inhibition was dependent upon the pre-treatment time.

In Vivo Assays

Assay: Assay (Method) for TPA-induced Inflammation

Animals:

Male Balb/c inbred mice were obtained from Charle River Breeding Laboratories (Kingston, N.Y.). Within a single experiment mice (22–25 g) were age-matched. These in vivo experiments typically involved use of 5–6 animals/group.

TPA-induced Mouse Ear Inflammation:

Assay of Ear-Edema:

TPA (12-O-tetradecanoylphorbol 13-acetate) (Sigma Chemical Company) in acetone (4 mg/20 ml) was applied to the inner and outer surfaces of the left ear of BALB/c male mice. The thickness of both ears was then measured with a dial micrometer (Mitutoyo, Japan) at both 2 and 4 hours after treatment, and the data expressed as the change in thickness ($10^{-3}$ cm) between treated and untreated ears. The application of acetone did not cause an edematous response; therefore, the difference in ear thickness represented the response to the TPA. After measuring the edema, the inflammed left ears were removed and stored at −70° C. until they were assayed for MPO (myeloperoxidase) activity where appropriate.

Assay of Myeloperoxidase (MPO) in Inflamed Ear Tissue:

On the day of the assay, partially thawed ear tissues were minced and then homogenized (10% w/v) with a Tissumnizer homogenizer (Tekmar Co.) in 50 mM phosphate buffer (pH 6) containing 0.5% HTAB. The tissue homogenates were taken through three cycles of freeze-thaw, followed by brief sonication (10 sec). The method of Bradley et al. was used with modifications as described. The appearance of a colored product from the MPO-dependent reaction of o-dianisidine (0.167 mg/ml; Sigma) and hydrogen peroxide (0.0005%; Sigma) was measured spectrophotometrically at 460 nm. Supernatant MPO activity was quantified kinetically (change in absorbance measured over 3 min, sampled at 15-sec intervals) using a Beckman DU-7 spectrophotometer and a Kinetics Analysis package (Beckman Instruments, Inc.). One unit of MPO activity is defined as that degrading one micromole of peroxide per minute at 25° C.

Statistics:

Statistical analysis was done using Student's "t" test. The $ED_{50}$ are values which cause a 50% inhibition of the inflammatory response and are calculated by regression analysis of the dose response data.

As shown below in Table 1, a representative compound of Formula (I), (3S,4R)-4-(isobutenyloxy)-3-(triphenylmethylamino)azetidin-2-one, Example 24 demonstrated positive activity in this assay.

TABLE 1

Effects of topically administered compounds on phorbol ester-induced inflammation in mouse ear.

| Compound | Edema @ 4 hr $ED_{50}$ (mg/ear) | MPO response $ED_{50}$ (mg/ear) |
|---|---|---|
| CoA-IT Example 24 | 0.49 | 0.48 |
| Steroid dexamethasone | 0.06 | 0.03 |

Balb/c mice were given PMA followed by the test compound. The edematous response was measured using a thickness gauge 4 hrs post PMA application. The animals were sacrificed and the inflamed ears harvested and MPO extracted and assayed spectrophotometrically as described in methods. Both compounds produced effects significantly different from vehicle treatment.

The positive activity of the compounds of Formula (I) in this animal model demonstrate a clear utility in the treatment of topically administered diseases associated with inflammation as noted herein such as, but not limited to, inflammatory bowel disease, contact dermatoses, actinic keratosis, psoriasis, or conjunctivitis.

As used herein, various abbreviations and explanations are as follows: [$^3$H], a molecule that contains tritium atoms, a radioactive isotope; A23187, a compound that allows free entry of calcium into a cell; AA, arachidonic acid, 5-8-11-14 eicosatetraenoic acid; arachidonate, arachidonic acid contained within a phospholipid; free arachidonic acid, arachidonic acid that is not contained within a phospholipid; [$^2$H$_8$]arachidonic acid, the form of arachidonic acid labeled with 8 deuterium atoms, a stable isotope; 1-alkyl, 1-O-alkyl; 1-alkenyl, 1-O-alk-1'-enyl; BSA, bovine serum albumin; CoA, coenzyme A; CoA-IT, CoA-independent transacylase; COX, cyclooxygenase; DTT, dithiothreitol; EGTA, [ethylenebis(oxyethylenenitrilo)]tetra acetic acid, a calcium chelator; GPC, sn-glycero-3-phosphocholine; EDTA, a metal ion chelator; GPE, sn-glycero-3-phosphoethanolamine; GC/MS, gas chromatography and mass spectrometry; 5HETE, 5(S)-hydroxyeicosa-6,8,11,14-tetraenoic acid; 15HETE, 15(S)-hydroxyeicosa-5,8, 11,13-tetraenoic acid; HL-60, American Type Tissue Culture designated cell line similar to a monocyte; 5LO, 5-lipoxygenase; LTB$_4$, leukotriene B$_4$; LTC$_4$, leukotriene C$_4$; LTD$_4$, leukotriene D$_4$; lyso PAF, 1-alkyl-2-lyso-GPC, lyso platelet-activating factor; PLA$_2$, phospholipase A$_2$; PBS, phosphate buffered saline; PAF, platelet activating factor, 1-alkyl-2-acetyl-GPC; PL, phospholipid; PC, phosphatidylcholine; PE, phosphatidylethanolamine, PI, phosphatidylinositol; PMN, polymorphonuclear neutrophilic cell, neutrophil; PS phosphatidylserine; Rf, the distance a compound travels as a fraction of the solvent front; TLC, thin layer chromatography; U937, American Type Tissue Culture designated cell line similar to a monocyte.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method for treating disease or disorders mediated by a lipid inflammatory mediator selected from arachidonric acid, its metabolites or platelet activating factor (PAF), which method comprising administering to a mammal in need thereof an effective Coenzyme A independent transacylase (CoA-IT) inhibiting amount of a compound of the Formula:

wherein
Y is NH;
X is O or S(O)m;
m is 0 or an integer having a value of 1, or 2;
R$_3$ is optionally substituted triphenylmethyl;
R$_4$ is optionally substituted C$_{1-10}$ alkyl, (CR$_{10}$R$_{20}$)$_n$C(R$_{10}$)=C(R$_7$)$_2$, or (CR$_{10}$R$_{20}$)n—C≡C—R$_5$;
n is an integer having a value of 1 to 4;
R$_{10}$ and R$_{20}$ are independently hydrogen or C$_{1-4}$ alkyl;
R$_5$ is hydrogen, alkyl, aryl, arylalkyl, heteroaryl, heteroarylalkyl, C(O)$_2$R$_6$, or C(O)R$_6$ wherein the alkyl, aryl, arylalkyl, heteroaryl, and heteroarylalkyl moieties may be optionally substituted;
R$_6$ is C$_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;
R$_7$ is independently hydrogen, C$_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;
or a pharmaceutically acceptable salt thereof.

2. The method according to claim 1 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in at least part by lipid inflammatory mediators.

3. The method according to claim 1 wherein R$_4$ is an optionally substituted C$_{1-10}$ alkyl, or alkenyl.

4. The method according to claim 3 wherein the alkyl is substituted by a ketal or thioketal.

5. The method according to claim 1 wherein R$_5$ is hydrogen, C(O)$_2$R$_6$ or a heteroaryl ring.

6. The method according to claim 5 wherein the heteroaryl ring is a pyridyl ring.

7. The method according to claim 1 wherein the compound, or a pharmaceutically accetable salt thereof, is:
(3RS,4RS)-4-(Isobutoxy)-3-(triphenylmethylamino) azetidin-2-one
(3R,4R)-4-(Isobutoxy)-3-(triphenylmethylamino)azetidin-2-one
(3S,4S)-4-(Isobutoxy)-3-(triphenylmethylamino)azetidin-2-one
(3R,4R)-4-(Isobutylthio)-3-(triphenylmethylamino) azetidin-2-one
(3R,4R)-4-(Isobutylsulfonyl)-3-(triphenylmethylamino) azetidin-2-one
(3S,4R)-4-(Isobutoxy)-3-(triphenylmethylamino)azetidin-2-one
(3S,4R)-4-(Propoxy)-3-(triphenylmethylamino)azetidin-2-one
(3S,4S)-4-(Propoxy)-3-(triphenylmethylamino)azetidin-2-one
(3S,4R)-4-(Benzyloxy)-3-(triphenylmethylamino)azetidin-2-one (3S,4S)-(Benzyloxy)-3-(triphenylmethylamino)azetidin-2-one
(3S,4R)-4-Methoxy-3-(triphenylmethylamino)azetidin-2-one
(3S,4R)-4-(Isobutenyloxy)-3-(triphenylmethylamino)azetidin-2-one
(3S,4R)-4-Octyloxy-3-(triphenylmethylamino)azetidin-2-one
(3S,4R)-4-Phenoxy-3-(triphenylmethylamino)azetidin-2-one
(3S,4S)-4-Phenoxy-3-(triphenylmethylamino)azetidin-2-one
(3S,4R)-3-[[(4-Iodophenyl)diphenylmethyl]amino]-4-(isobutoxy)azetidin-2-one
(3S,4S)-4-[3-(Methoxycarbonyl)propoxy]-3-(triphenylmethylamino)azetidin-2-one
(3S,4R)-4-[[2-(3-Pyridylmethyl)-1,3-dithian-2-yl]methoxy]-3-(triphenylmethylamino)-azetidin-2-one
(3S,4S)-4-(Prop-2-ynyloxy)-3-(triphenylmethylamino)azetidin-2-one
Methyl 4-[(3S,4S)-2-oxo-3-(triphenylmethylamino)azetidin-4-yloxy]but-2-ynoate
Methyl 4-[(3S,4R)-2-oxo-3-(triphenylmethylamino)azetidin-4-yloxy]but-2-ynoate
(3S,4R)-4-[(2(5 H)Furanon-4-yl)methoxy]-3-(triphenylmethylamino)azetidin-2-one
(S)-3-(Triphenylmethylamino)azetidin-2-one
(RS)-3-(Triphenylmethylamino)azetidin-2-one; or
(3R,4R)-4-(Methylsulfonyl)-3-(triphenylmethylamino)azetidin-2-one.

8. A method for treating an inflammatory disease or disorder in a mammal in need thereof which method comprises administering to said mammal an effective amount of a compound of Formula (I)

wherein
Y is NH;
X is O or S(O)m;
m is 0 or an integer having a value of 1, or 2;
$R_3$ is optionally substituted triphenylmethyl;
$R_4$ is optionally substituted $C_{1-10}$ alkyl, $(CR_{10}R_{20})_nC(R_{10})=C(R_7)_2$, or $(CR_{10}R_{20})n—C≡C—R_5$;
n is an integer having a value of 1 to 4;
$R_{10}$ and $R_{20}$ are independently hydrogen or $C_{1-4}$ alkyl;
$R_5$ is hydrogen, alkyl, aryl, arylalkyl, heteroaryl, heteroarylalkyl, $C(O)_2R_6$, or $C(O)R_6$ wherein the alkyl, aryl, arylalkyl, heteroaryl and heteroarylalkyl moieties may be optionally substituted;
$R_6$ is $C_{1-10}$ alkyl, aryl, arylalkyl, heteroaryl, heteroarylalkyl, heterocyclic, or heterocyclicalkyl, all of which may be optionally substituted;
$R_7$ is independently hydrogen, $C_{1-10}$ alkyl, aryl, arylalkyl, heteroaryl, heteroarylalkyl, heterocyclic, or heterocyclicalkyl, all of which may be optionally substituted;
or a pharmaceutically acceptable salt thereof.

9. A compound of the formula:

(Ia)

wherein
Y is NH;
X is O or S
$R_3$ is optionally substituted triphenylmethyl;
$R_4$ is optionally substituted $C_{1-10}$ alkyl, $(CR_{10}R_{20})_nC(R_)=C(R_7)_2$, or $(CR_{10}R_{20})n—C≡C—R_5$;
n is an integer having a value of 1 to 4;
$R_{10}$ and $R_{20}$ are independently hydrogen or $C_{1-4}$ alkyl;
$R_5$ is hydrogen, alkyl, aryl, arylalkyl, heteroaryl, heteroarylalkyl, $C(O)_2R_6$, or $C(O)R_6$ wherein the alkyl, aryl, arylalkyl, heteroaryl, and heteroarylalkyl moieties may be optionally substituted;
$R_6$ is $C_{1-10}$ alkyl, aryl, arylalkyl, heteroaryl, heteroarylalkyl, heterocyclic, or heterocyclicalkyl, all of which may be optionally substituted;
$R_7$ is independently hydrogen, $C_{1-10}$ alkyl, aryl, arylalkyl, heteroaryl, heteroarylalkyl, heterocyclic, or heterocyclicalkyl, all of which may be optionally substituted;

excluding 4-methoxy-3-(triphenylmethylamino)azetidin-2-one,
4-(isobutenyloxy)-3-(triphenylmethylamino)azetidin-2-one, 4-(methylsulfonyl)-3-(triphenylmethylamino)azetidin-2-one, and 4-(prop-2-ynyloxy)-3-(triphenylmethylamino)azetidin-2-one;
or a pharmaceutically acceptable salt thereof.

10. The compound according to claim 9 wherein $R_4$ is an optionally substituted $C_{1-10}$ alkyl or alkenyl.

11. The compound according to claim 10 wherein the alkyl is substituted by a ketal or thioketal.

12. The compound according to claim 9 wherein $R_4$ is $(CR_{10}R_{20})n—C≡C—R_5$; and $R_5$ is hydrogen, $C(O)_2R_6$ or a heteroaryl ring.

13. The compound according to claim 12 wherein the heteroaryl ring is a pyridyl ring.

14. A pharmaceutical composition comprising a pharmaceutically acceptable diluent or carrier and a compound according to claim 9.

15. A pharmaceutical composition comprising a pharmaceutically acceptable diluent or carrier and (3S,4R)-4-(isobutenyloxy)-3-(triphenylmethylamino)azetidin-2-one, or a pharmaceutically acceptable salt thereof.

* * * * *